United States Patent [19]

Gonser et al.

[11] Patent Number: 4,582,998
[45] Date of Patent: Apr. 15, 1986

[54] APPARATUS AND METHOD FOR LIGHT CURING MEDICAL AND PROSTHETIC OBJECTS

[75] Inventors: Donald I. Gonser; George T. Eden; Louis H. Tateosian, all of York, Pa.

[73] Assignee: Dentsply Research & Development Corp., Milford, Del.

[21] Appl. No.: 596,611

[22] Filed: Apr. 6, 1984

Related U.S. Application Data

[63] Continuation-in-part of Ser. No. 492,284, May 6, 1983.

[51] Int. Cl.$^4$ ................................................. G01J 1/00
[52] U.S. Cl. .............................. 250/492.1; 250/503.1; 250/494.1
[58] Field of Search ........... 250/493, 494, 495, 504 R, 250/492.1, 503.1

[56] References Cited

U.S. PATENT DOCUMENTS

| | | |
|---|---|---|
| 757,806 | 4/1904 | Giersiepen ................... 250/455.1 |
| 1,109,206 | 9/1914 | Dexheimer et al. |
| 1,277,111 | 8/1918 | Patterson |
| 1,954,591 | 4/1934 | Keith et al. |
| 1,960,534 | 5/1934 | Gibney |
| 3,258,585 | 6/1966 | Crete |
| 3,375,362 | 3/1968 | Klippert |
| 3,648,706 | 3/1972 | Holzer |
| 3,887,801 | 6/1975 | Hzig et al. |
| 3,952,322 | 4/1976 | Wolfe |
| 4,025,778 | 5/1977 | Havakawa |
| 4,298,005 | 11/1981 | Mutzhas ...................... 250/504 R |
| 4,412,134 | 10/1983 | Herold et al. ............... 250/504 R |
| 4,421,987 | 12/1983 | Herold ........................ 250/504 R |

FOREIGN PATENT DOCUMENTS 2098439 11/1982 United Kingdom.

Primary Examiner—Bruce C. Anderson
Attorney, Agent, or Firm—Woodcock Washburn Kurtz Mackiewicz & Norris

[57] ABSTRACT

Apparatus and method for providing light curing of prostheses and other medical object materials, the object being prefabricated of a material which is hardened, or polymerized when exposed to visible light. An array of light sources is provided relative to a rotatable platform on which the object is placed, each light source providing a substantially collimated light beam and directed to optimally intercept the rotating object. There are preferably four such light sources, each having a visible light bandpass characteristic and directed at an angle within 25°-45° of the platform surface, the light beams being directed at the platform surface in overlapping fashion so as to provide continuous incident light on the object during each cycle of rotation.

19 Claims, 3 Drawing Figures

APPARATUS AND METHOD FOR LIGHT CURING MEDICAL AND PROSTHETIC OBJECTS

CROSS REFERENCE TO RELATED APPLICATION

This is a continuation-in-part of pending U.S. application Ser. No. 492,284, filed May 6, 1983, assigned to the same assignee.

FIELD OF THE INVENTION

This invention relates to apparatus and method for visible light curing, and in particular an apparatus and method for visible light curing of medical, prosthetic and like objects which have been fashioned of light curable material of the sort which enables total curing within a matter of minutes.

BACKGROUND OF THE INVENTION

Light curing apparatus and techniques, as have been used in dental applications to date, have been directed primarily to the use of light curing of restorative materials, such as in oral cavities. In such applications, which have been reasonably successful, a light source is positioned at or substantially at contact with the material to be cured, such that a highly focused or condensed beam of light is directed on a relatively small area of curable material. For example, assignee's Prisma Lite system employs a light gun, or applicator as shown in U.S. Pat. No. 4,385,344. Prior to this visible light application, UV curable materials and UV sources had been used in the dental industry. Generally, such dental applications have been limited to small localized fillings and the like.

In the field of fabricating prosthetics, dentures and the like, little work has been done heretofore in the use of light polymerizable or curable materials. However, recent technique and material developments for dental prosthetic and restorative work have made it feasible to produce dentures much more quickly and reliably than has been done in the prior art. These new techniques and methods for making artificial teeth can be used by dentists and/or dental laboratories to fabricate dentures and restorations, and can be extended to the making of medical prosthetics and devices, or portions thereof, e.g., custom made hearing aids, maxio-facial prostheses, cranial prostheses, and other objects such as custom-formed shoe inserts.

The operation of light curing a denture or prosthetic bridge presents certain problems which are not encountered using more conventional methods. However, once solved the light curing operation permits a much more efficient denture making process. Any satisfactory apparatus for light curing of dentures requires a substantial depth and degree of curing, much more than for curing coatings. Dentures come in vastly different sizes and shapes, and the penetration requirements vary with the size and configuration. A standarized light source apparatus for curing dentures needs to provide light of an intensity to be safely above the zone of reciprocity failure, i.e., the zone below which curing is not achieved no matter how long light is applied. Further, an apparatus and method is needed which ensures that light is incident at all possible angles onto all features of the denture, so that all portions of the material are light penetrated and cured. Thus, there is a great demand placed upon any proposed apparatus and technique for photocuring a wide range of sizes and shapes of restorative objects, which apparatus must be safe for people working in the immediate area, and which must operate with a sufficient efficiency to minimize apparatus bulk and expense, thereby ensuring low maintenance and maximum reliability of operation. With the provision of such apparatus, dentures can be cured in a matter of minutes, which is a highly substantial advance over the prior capability of the industry.

SUMMARY OF THE INVENTION

It is an object of this invention to provide an apparatus and method for photocuring of medical and dental objects such as dentures, cranial prostheses, dental bridges, and other prostheses, in a relatively short period of time.

It is another object of this invention to provide a method of visible light curing of a medical article such as a prosthetic object or portion thereof, the prosthetic object being composed at least in part of a light curable material.

It is another object of this invention to provide apparatus for curing a medical object or portion of a medical device composed at least in part of light curable material, by efficiently exposing all portions of the object or portion thereof to light radiation, which radiation is supplied at a power sufficient to thoroughly penetrate and cure throughout the object or portion.

It is another object of this invention to provide an apparatus and a method of photocuring of a wide range of medical object sizes and shapes, and to do so efficiently and reliably in a minimum amount of time.

It is another object of this invention to provide apparatus for photocuring of prosthetic objects, and like medical objects, which apparatus is safe for persons working in the environment.

It is another object of this invention to provide standarized apparatus which is relatively inexpensive and maintenance free, and which is adapted to be used by in medical laboratories or hospitals for controlled and timed photocuring of medical objects.

In accordance with the above objects, there is provided a visible light curing apparatus having a rotatable support means, e.g. a table or, platform for supporting an item or object composed at least in part of light curable material, and an array of one or more collimated light sources positioned to direct beams of collimated light from different angles on to the support means, and thus onto the item or object which is placed on the support means. Each of the light sources, which preferably include a tungsten halogen lamp with a parabolic reflector, is positioned at a respective angle relative to the support axis and at a predetermined angle relative to the surface plane of the support means, the lights providing overlaping light coverage of the entire support surface. The invention comprises exposing a medical object such as a prosthetic device which is placed on the support means to the collimated light beams, for at least a predetermined amount of time, and rotating the object relative to the lights to vary the angle of incidence of light on all features and surfaces thereof, thereby ensuring complete curing within all portions of the material. The light sources are filtered to provide a spectral content with a bandpass of wavelengths in the 350–600 nm range, and most particularly in the 400–500 nm range and other wavelengths produced are greatly antenuated.

DESCRIPTION OF THE PREFERRED EMBODIMENT

Figure 1:
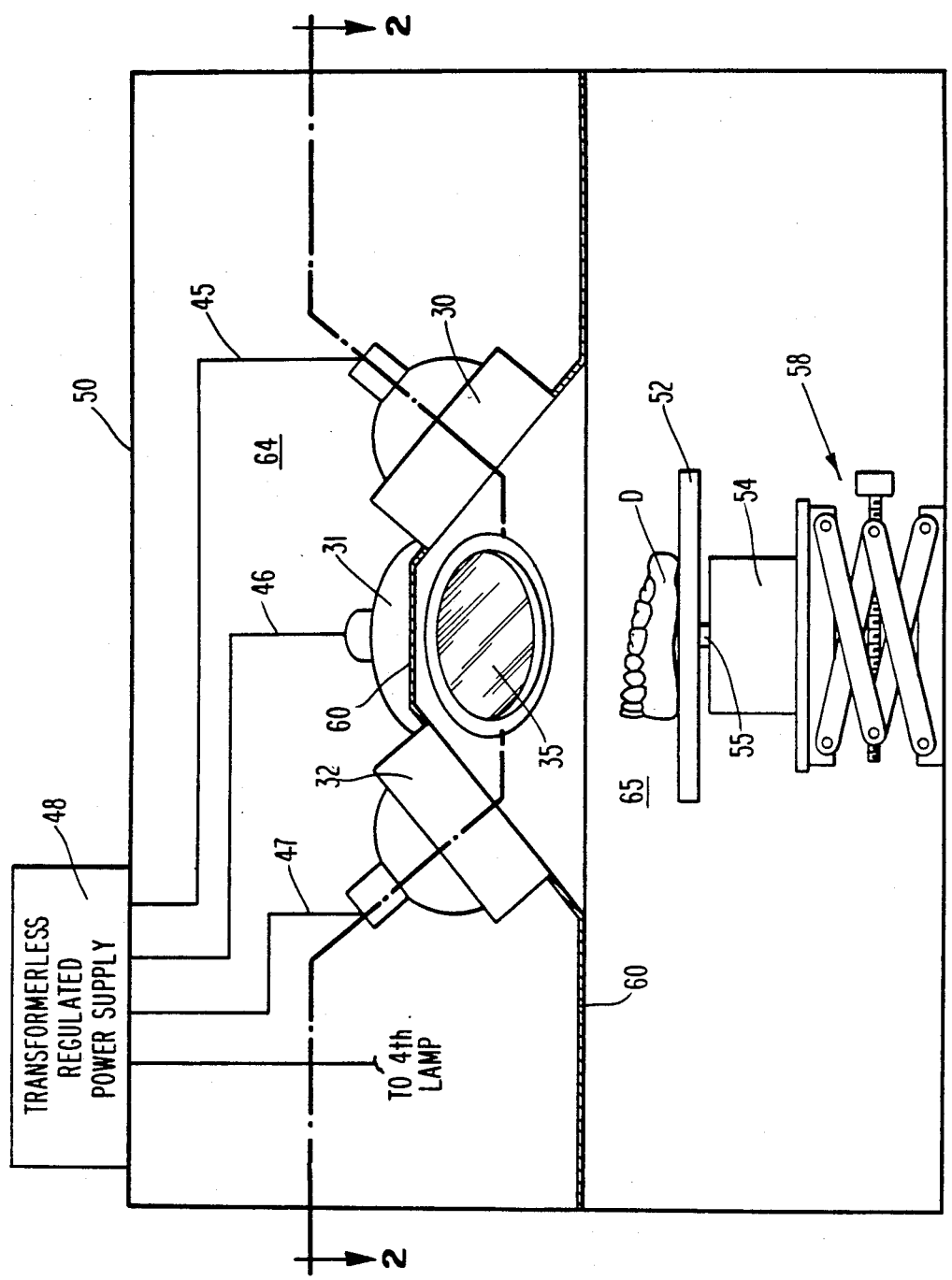
FIG. 1 is a side schematic view of the apparatus of this invention, showing the positioning of the lamps with respect to the rotatable table on which the object, for example a denture, is placed.
Figure 2:
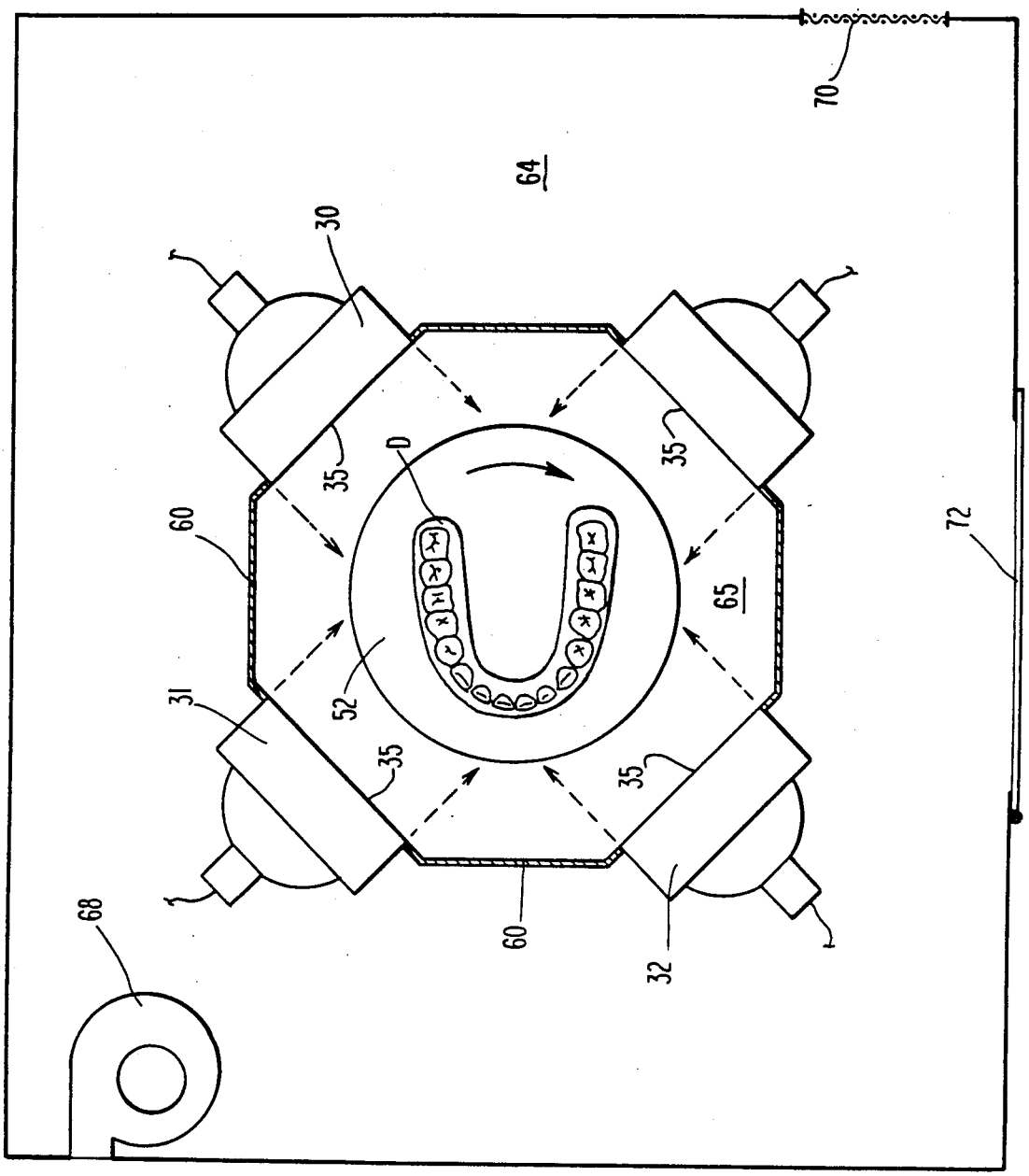
FIG. 2 is a top schematic view of the apparatus used in the practice of this invention, along lines 2—2, further illustrating the placement of the lamps, a still air chamber where the object is light irradiated and a circulating air chamber wherein the heat from the back of the lamps and reflectors is carried away.

Referring now to FIGS. 1 and 2, there is seen apparatus for light curing of a relatively large size restorative object such as a denture. A denture, designated D, is shown positioned on a rotatable table 52. The denture is made of a suitable base material such as disclosed in co-pending U.S. application Ser. No. 486,688, titled "Organic Amine Salt of An Acid, Manufacture and Use As Accelerator", assigned to the same assignee. While the drawings illustrate a denture as the object being cured, it is to be understood that the invention relates broadly to the curing of medical objects of any sort, including particularly prostheses, portions of medical devices that must be custom shaped or contoured, and medical assist devices such as custom-formed shoe inserts.

Positioned to direct beams of collimated light at the table 52, and thus at a denture D placed thereon, is a collimated light source means comprising one or more lamps, or light sources. In the preferred embodiment of this invention, four such lamps are used. In FIG. 1, lamps 30, 31 and 32 are shown positioned relative to the table 52. FIG. 2 illustrates four lamp surfaces 35, positioned at approximately 90° intervals around the center axis of table 52. The lamp outputs are directed through surfaces, or faces 35, which in the preferred embodiment are about 2⅜ inches in diameter. The light output from each lamp is collimated, and thus casts a light beam of about 2⅜ inches diameter onto the table 52. The lamps are tilted such that the axis of each light beam is at an angle within the range of about 20°–45° from the horizontal surface of table 52. The preferred angle is about 30°. Further, the lamps are directed so that all portions of the table 52, or denture D resting thereon, are irradiated, the light beams having overlaping portions. By this means, wherever the denture is positioned on the table, during the course of each rotation light will be incident on the denture so as to penetrate to all portions thereof.

Figure 3:
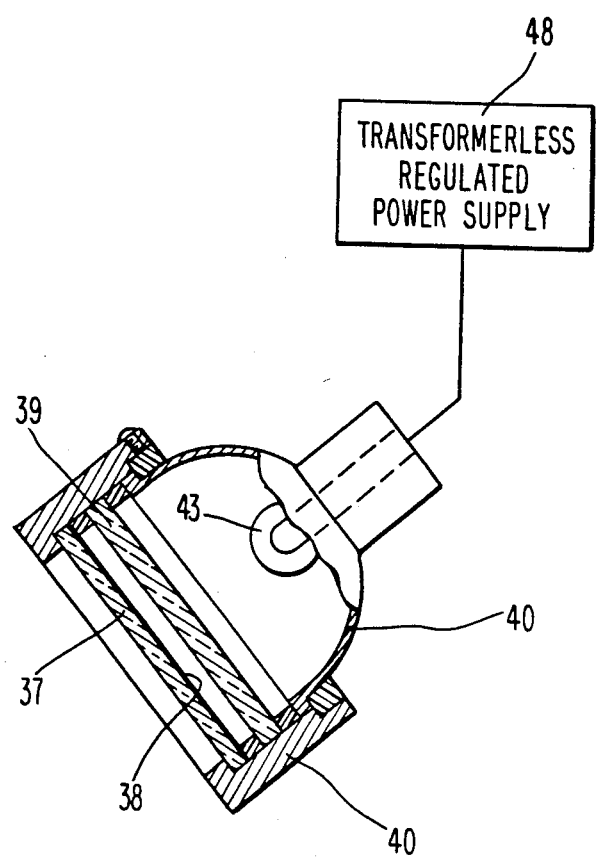
FIG. 3 is a detail view of a light source used.

As seen in detail in FIG. 3, each light means has a parabolic reflector 40, and a bulb or lamp 43 positioned at the center thereof. The lamp is preferably a tungsten halogen bulb, but other types of bulbs may be used. In the preferred embodiment, the lamp is driven by a transformerless regulated power supply 48, which also contains suitable timing means for timing the length of turn on of each lamp. The lamps are designed for rated power of 200 watts and 41 volt operation, and preferably are operated at about −20% of rated voltage, or 32.8 volts. At this voltage, each lamp delivers about 54.7 mw/cm$^2$ of light in the 400–500 bandwidth, at a distance of about 10 cm, i.e. the distance from the center of the light surface 35 to the center of the table. Each light means also contains a bandpass filter 37, having a heat reflecting film 38 on the bulb side thereof, and a heat absorbing filter 39.

As seen in FIG. 1, leads 45, 46 and 47, from the three light sources illustrated, are connected through the top of housing 50 to the power supply 48. A like lead is provided to the fourth lamp, and if five or more lamps are utilized they are powered in the same manner. The table 52 is rotated by a motor 54 which drives shaft 55 which is connected through to the table. In practice, the speed of rotation of the table is not believed critical, but it has been found that a range of about 0.5 to 50 rpm is suitable and about 2 rpm is a preferred speed. Further means 58 are employed to raise or lower the table 52, which may be necessary to accommodate dentures of mounted on models of different sizes. It has been found that a 4 inch diameter table is suitable to accommodate any anticipated denture size. For other applications involving curing of prosthetic objects, a larger table is used. Depending upon the height of the table, the lamps, which are fixed in position, may be within a range of 5 to 13 cm from the surface of the denture or object of similar size, and on the average the distance from the rim of each light source to the center of the table is about 10 cm. For larger medical or medical-related objects, a greater average distance is utilized.

While the preferred embodiment of a rotatable table is disclosed, the invention embraces any means for moving the object to be cured relative to the light source means, e.g. the lights may be moved, or the table can be moved through a different cycle, which may include raising and lowering as well as rotating.

Still referring to FIGS. 1 and 2, there is shown an enclosure 60, preferably made of sheet metal, which encloses an upper chamber 64 within the overall housing 50. The table 52 and denture D are in a region 65, which is accessible through a door 72. The enclosure wall 60 has circular openings into which the faces 35 of the light sources are positioned. The lamps are connected to the sheet metal 60 with suitable mounting and connecting means, so as to provide a substantially air tight separation between spaces 64 and 65. As illustrated in FIG. 2, a fan or other air circulating means 68 is provided, along with one or more vents 70, to provide positive or negative pressure for air cooling of the light sources. The enclosure 60 provides that the air circulation, which is necessary for cooling, does not affect the environment where the denture is, thereby keeping it free of circulating dust particles or other elements which could be detrimental to proper curing and formation of the denture.

The curing unit of the present invention also may incorporate a housing 50 having walls or doors 72 that are visually transparent to allow inspection during operation of the unit in a closed operating mode. It is important for maintenance purposes that an operator be able to observe whether the lamps are operating. The transparent door, wall or wall portions may form one of the safety filters for protection of the operator's eyes while allowing a clear view of the unit's exact operation for precision of operation, particularly where a remake is involved caused by an operation caused flaw. The filtering arrangement also eliminates the emission of dangerous light waves such as UV waves.

In practice, whenever the denture or medical object has been formed of the light curable material, the operator opens door 72 in the housing 50, and places the denture on the table 52. The operator then sets a timer, which is part of the apparatus in the box designated 48, and energizes the system for the programmed time of curing. In the preferred embodiment, the transformerless power supply 48 is as shown in co-pending application, titled Power Control Apparatus With Optical Isolation Feedback Means, D-154, U.S. Ser. No. 492,285, assigned to the same assignee and incorporated herein by reference. A soft start of power supplied to the lamps is provided, i.e. the voltage is ramped up to the designated power. By operating at about 20% less than rated value, a relatively long lifetime of about 600 hours can be obtained for the lamps used in the preferred embodiment.

In practice, the lamps may have a rating in the range of 30-60 volts, and may be operated at 10 to 25% reduction of rated voltage. Depending upon the size of the object to be cured, the operator adjusts the level of table 52 appropriately. As the object is rotated, light from each of the four light sources is incident thereon at continuously different angles, such that all portions of the object are irradiated. By holding the lamps within about 10 cm from the object surface, and providing collimated beams with a diameter of at least about 2 inches and a beam power of at least about 50 mw/cm$^2$ at the denture, there is more than sufficient light power to thoroughly penetrate and cure all portions of the object.

As used in this specification and the claims hereto, the term "object" or "medical object" means any object which is shaped and then light cured for use in a medical or medically related application, or any portion of such an object, or any portion of a device used in any medical or medically related application. Also, it is to be understood that the phrase collimated light refers to a beam of light having light flux lines which are substantially parallel, it being understood that it is physically impossible to generate a precisely and totally collimated beam. The simple parabolic reflector as used in the apparatus of this invention provides a beam which is sufficiently collimated that there is relatively little loss of light flux from the light source face 35 to the position of the denture, i.e. there is relatively little loss over the beam distance of 5-13 cm. Further, while the lamp which is preferred for use in the apparatus of this invention has a rated voltage of 41 volts, and a rated power of about 200 watts, and these parameters have been found to provide excellent results, the lamps can be designed for different power and voltage ratings within the scope of this invention. Likewise the power supply can be a conventional power supply utilizing a transformer or other design. However, it is noted that the combination of all of the design parameters as has been set forth herein contribute to an overall system and method which has been found to be unusually efficient for the stated purpose of curing dentures and like objects, and the parameters as disclosed and claimed are preferred for the practice of this invention.

In carrying out the method of this invention, the object is placed under the light for a time of about ½ to 15 minutes, during which the object is moved cyclically relative to the lamp or lamps. Collimated light is directed onto the object at the preferred angle, from a distance of about 10 cm and with a power at the object surface of at least about 50 mw/cm$^2$. Based on visual observations of a denture undergoing light curing, improved direct light penetration is achieved. Also, visual observation has revealed that there is light curing of shaded areas, i.e. areas shaded by opaque material. This is believed to result from scattering of light rays that, due to the collimated light, have penetrated deeply into the translucent denture material.

In some embodiments, it may be desirable to equip the curing chamber 65 with air circulating means in the general manner disclosed with respect to chamber 64, or the two chambers may be interconnected.

From all of the above, it will be understood that a method is provided for curing medical objects having light curable material as their composition or a portion of their composition. The object is engaged with a support and the light curable material is positioned for curing by projecting collimated light on it.

It is preferred to project the light onto the curable material from a plurality of light sources positioned at different degree settings of an imaginary 360° circle. As shown in FIG. 2, the lamps 30, 31, 32 and 33 are positioned one in each of the four 90° quadrants of an imaginary 360° circle around the object D. The circle is envisioned as extending around the object in a horizontal plane. The light sources or lamps are preferably positioned in at least three of the quadrants and preferably positioned so that all quadrants of the imaginary 360° circle are simultaneously projected with light at the periphery of the light curable material.

The light sources are preferably aimed with the center of the projected light from each light source approximately crossing an imaginary line corresponding with the average vertical height or the outer peripheral massive positions of the light curable material. By massive portions, it is meant to eliminate distortions in position due to small thin projecting portions which, in general, would not be expected to exhibit severe curing problems. The projected light is preferably projected at an angle of 20° to 45° from an imaginary horizontal plane taken at the lowermost portion of light curable material which corresponds to the top surface of the Table 52 in FIG. 1.

Preferably the light curable material is positioned for curing by adjusting the height of the support or Table 52. The table is preferably rotated as previously discussed.

To achieve the depth of penetration providing the best results in thick objects, the light should be of high intensity in the activation wavelength region. High intensity light is further important to compensate for the loss of cure efficiency on the cured object surface by oblique incident light.

While a source of high intensity light in the activation band is indicated, the adverse heating effects normally associated with such a source should be avoided on the article being cured to avoid damage in the usual instance. By adverse heating effects, it is meant quantitites of radiant heat that cause the article being cured to change shape due to heat induced flow or thermal expansion. The present invention avoids these adverse heating effects by heat absorption and reflection filters without substantial loss of light in the activation band.

The removal of red and infrared light rays in the wave length range between 700 nm and 2400 nm is important to limit because of heating that demonstrates an adverse effect on light sensitive materials if not properly filtered. If excess infrared energy is permitted in the collimated light beam, excessive temperature rise in the material may result, causing rapid changes in the material to reduce viscosity or if sufficiently high, results in decomposition of the material. Because of an excessive high temperature rise problem in material, optical filtering is important to reduce the red and infrared wave lengths between 700 nm and 2400 nm. For example, a 41 volt, 200 watt tungsten halogen lamp operated at −20% of its rated voltage or at 32.8 voltage having a 50 mm diameter parabolic reflector delivers a total of 35 watts at 6 cm distance from the reflector rim. In a preferred application of the invention, such as shown in FIG. 2, where four (4) lamps are used, the material receives about 140 watts of optical power from wave lengths that are present in the light beam between 700 nm and 2400 nm. A heat-reflecting filter placed in the optical beam path can be made to reflect or virtually remove wave lengths between 700 nm and 1100 nm. This reduces the power delivered from the parabolic reflector to 17.5 watts per lamp or a total of 70 watts delivered to the material using four (4) lamps. This is a 50% reduction in heating rays of the light beam. The addition of a second heat-absorbing filter is capable of removing wave lengths between 700 nm and 2400 nm and further reducing the red and infrared rays from the beam when used in conjunction with the heat reflecting filter to 1.4 watts or a total of 5.6 watts, using the four (4) lamps in the preferred application. This is a net reduction of 96% of the heating rays in the light beam delivered to the material.

The addition of a heat-absorbing filter only that is capable of removing wave lengths between 700 and 2400 nm reduces the red and infrared rays from the beam to 2.8 watts, or a total of 11.2 watts using four (4) lamps in the preferred application. This is a net reduction of 92% of the heating rays in the light beam delivered to the materials.

In special instances, some of the parameters previously delineated can be varied to advantage in preferred ranges. For example, the table may be rotated at from 0.5 to 50 rpm and the lamps or light source faces may be 1 to 15 cam, or more for large objects, from their closest approach to the surface to be cured.

It is an important aspect of the apparatus of the present invention that it is adapted for use in hospitals and other medical uses where special needs exist, as contrasted to industrial equipment. The use of collimated light enables operation with a minimum of heat, which provides for safer operation in medical applications. The apparatus and method further provide a greater amount of cure power with the least amount of infrared generation, and with a minimum amount of input power required. A further feature that enables operation at low power is the fact that with collimated light there is less scattering of the light, resulting in a higher efficiency utilization. Thus, the curing apparatus of this invention enables a compact light weight construction and operates at a relatively cool temperature, which is a substantial advantage in medical applications. Also, due to the minimized power requirements it can be operated from a standard 110 volt line.

We claim:

1. Visible light curing apparatus for curing medical objects, comprising
    support means defining a substantially horizontal surface having a center axis for supporting a medical object composed at least in part of light curable material; and
    an array of collimated light sources positioned to direct collimated light on said object, each of said sources being at a respective different angle relative to said support axis and at least one of said sources being positioned to direct collimated light on said medical object at an angle of 20°–45° toward the vertical from the plane of said horizontal surface, each said light source being positioned about 5–13 cm from about the center of said surface, said sources providing a substantially constant light flux of at least about 50 mw/cm$^2$ at the surface of the object being cured.

2. The apparatus as described in claim 1, wherein each of said light sources comprises an IR reflecting filter and a visible light bandpass filter, said bandpass filter passing wavelengths in the 350–600 nm range.

3. The apparatus as described in claim 2, wherein each of said light sources comprises a tungsten halogen lamp.

4. The apparatus as described in claim 1, wherein each of said light sources provides a collimated beam having a diameter of at least about 2 inches.

5. The apparatus as described in claim 1, wherein each of said light sources comprises a lamp having a power rating of at least about 175–200 watts, and wherein each said light source provides a beam of at least about 50 mw/cm$^2$.

6. The apparatus as described in claim 5, comprising a transformerless regulated power supply connected to power said array of light sources, and wherein each of said light sources is rated to operate with an applied voltage in the range of 30–60 volts.

7. The apparatus as described in claim 6, wherein said power supply provides a voltage to each of said lamps such that they each operate at about 10 to 25% less then rated power.

8. The apparatus as described in claim 6, wherein each of said lamps operates at about 41 volts.

9. The apparatus as described in claim 1, comprising moving means for providing relative movement of the surface of said support means relative to said light array.

10. The apparatus as described in claim 9, wherein said moving means comprises rotating means for rotating said support means about said axis.

11. The apparatus as described in claim 10, wherein said rotating means rotates said support means at about 5–25 rpm.

12. The apparatus as described in claim 1, wherein said array comprises four light sources positioned at approximately 90 intervals around said support means axis.

13. The apparatus as described in claim 1, wherein each of said light sources directs a beam at an angle within a range of about 20–45% from said horizontal surface.

14. The apparatus as described in claim 1, comprising a housing within which said apparatus is housed, an enclosure means for creating a still air chamber within which said support means is positioned, and a circulating air chamber containing air circulation means so as to cool said light sources, said enclosure having openings into which are mounted the faces of each of said light sources.

15. The apparatus as described in claim 9, wherein said moving means comprises means for moving the height of said support surface.

16. Light curing apparatus for curing of medical objects, comprising
    a support surface for supporting a said object, and means for cyclically rotating said support surface;
    an array comprising a plurality of light sources, each of said sources providing a beam of collimated light directed toward said support surface, at least one of said sources being positioned to direct light at said surface at an angle of 20°–45° toward the vertical from the plane of said surface said array providing a light density of at least about 50 mw/cm² at said surface, and mounting means for mounting said light sources so that each said source has its output within about 15 cm from said support surface.

17. The apparatus as described in claim 16, wherein each of said lights is positioned to direct its beam at said surface at an angle of about 25°–45° from said surface.

18. The apparatus as described in claim 16, wherein each said source output is about 10 cm from the center of said surface.

19. The apparatus as described in claim 16, wherein said light sources are positioned so that said beams are directed onto said surface in a partially overlapping manner.

* * * * *